US010626141B2

(12) United States Patent
Izumi et al.

(10) Patent No.: US 10,626,141 B2
(45) Date of Patent: Apr. 21, 2020

(54) METHOD FOR SPECIFIC CLEAVAGE OF C ALPHA-C BOND AND SIDE CHAIN OF PROTEIN AND PEPTIDE, AND METHOD FOR DETERMINING AMINO ACID SEQUENCE

(71) Applicants: SHIMADZU CORPORATION, Kyoto-shi, Kyoto (JP); NATIONAL UNIVERSITY OF CORPORATION HIROSHIMA UNIVERSITY, Higashihiroshima-shi, Hiroshima (JP)

(72) Inventors: Shunsuke Izumi, Higashihiroshima (JP); Koichi Tanaka, Kyoto (JP); Yuko Fukuyama, Kyoto (JP)

(73) Assignees: SHIMADZU CORPORATION, Kyoto (JP); NATIONAL UNIVERSITY OF CORPORATION HIROSHIMA UNIVERSITY, Hiroshima (JP)

( * ) Notice: Subject to any disclaimer, the term of this patent is extended or adjusted under 35 U.S.C. 154(b) by 114 days.

(21) Appl. No.: 15/594,461

(22) Filed: May 12, 2017

(65) Prior Publication Data

US 2017/0327533 A1    Nov. 16, 2017

(30) Foreign Application Priority Data

May 16, 2016   (JP) ................. 2016-098326

(51) Int. Cl.
*C07K 1/00*    (2006.01)
*C07K 1/12*    (2006.01)
(Continued)

(52) U.S. Cl.
CPC ............ *C07K 1/128* (2013.01); *C07C 205/59* (2013.01); *C07C 205/60* (2013.01);
(Continued)

(58) Field of Classification Search
CPC ................................................ C07K 1/128
(Continued)

(56) References Cited

U.S. PATENT DOCUMENTS

2006/0243899 A1*  11/2006  Matsuo ............. G01N 33/6842
                                                       250/282
2012/0276643 A1   11/2012  Takayama

FOREIGN PATENT DOCUMENTS

EP       1 739 419 A1      1/2007
JP       2005-326391 A    11/2005
(Continued)

OTHER PUBLICATIONS

Daiki Asakawa and Mitsuo Takayama "Fragmentation Processes of Hydrogen-Deficient Peptide Radicals in Matrix-Assisted Laser Desorption/Ionization In-Source Decay Mass Spectrometry" J. Phys. Chem. B 2012, 116, 4016-4023 (Year: 2012).*

(Continued)

*Primary Examiner* — Christopher Adam Hixson
*Assistant Examiner* — Emily R. Berkeley
(74) *Attorney, Agent, or Firm* — Wenderoth, Lind & Ponack, L.L.P.

(57) ABSTRACT

The present invention provides a method for specifically cleaving a Cα-C bond of a peptide backbone and/or a side chain of a protein and a peptide, and a method for determining amino acid sequences of protein and peptide. A method for specifically cleaving a Cα-C bond of a peptide backbone and/or a side chain bond of a protein or a peptide, comprising irradiating a protein or a peptide with laser light in the presence of at least one hydroxynitrobenzoic acid selected from the group consisting of 3-hydroxy-2-nitrobenzoic acid, 4-hydroxy-3-nitrobenzoic acid, 5-hydroxy-2-nitrobenzoic acid, 3-hydroxy-5-nitrobenzoic acid, and 4-hydroxy-2-nitrobenzoic acid. A method for determining an (Continued)

(D) 3H5NBA        (C) 5H2NBA        (B) 4H3NBA        (A) 3H2NBA (G) 1,5-DAN      (F) 5-NSA         (E) 4H2NBA amino acid sequence of a protein or a peptide, comprising irradiating a protein or a peptide with laser light in the presence of the above specific hydroxynitrobenzoic acid to specifically cleave a Cα-C bond of a peptide backbone and/or a side chain bond, and analyzing generated fragment ions by mass spectrometry.

5 Claims, 9 Drawing Sheets

Specification includes a Sequence Listing.

(51) Int. Cl.
  *G01N 33/68* (2006.01)
  *H01J 49/00* (2006.01)
  *C07C 205/59* (2006.01)
  *C07C 205/60* (2006.01)
(52) U.S. Cl.
  CPC ..... *G01N 33/6842* (2013.01); *G01N 33/6851* (2013.01); *H01J 49/0059* (2013.01)
(58) Field of Classification Search
  USPC .......................................................... 436/90
  See application file for complete search history.

(56) References Cited

FOREIGN PATENT DOCUMENTS

JP      2013-130570 A      7/2013
WO    WO-2011/007743 A1    1/2011

OTHER PUBLICATIONS

Extended European Search Report for the Application No. 17 17 0513 dated Sep. 19, 2017.

Asakawa, Daiki, "Principles of Hydrogen Radical Mediated Peptide/Protein Fragmentation During Matrix-Assisted Laser Desorption/Ionization Mass Spectrometry", Mass Spectrometry Reviews, 2014, vol. 35, pp. 535-556.

Asakawa, Daiki, "5-Nitrosalicylic Acid as a Novel Matrix for In-Source Decay in Matrix-Assisted Laser Desorption/Ionization Mass Spectrometry,"Mass Spectrometry, 2013, vol. 2, 11 pages.

Matsuo, Ei-ichi et al.,"Selective detection of 2-nitrobenzenesulfenyl-labeled peptides by matrix-assisted laser desorption/ionization-time of flight mass spectrometry using a novel matrix", Proteomics, 2006, vol. 6, pp. 2042-2049.

Sakakura, Motoshi et al.,"In-Source Decay and Fragmentation Characteristics of Peptides Using 5-Aminosalicylic Acid as a Matrix in Matrix-Assisted Laser Desorption/Ionization Mass Spectrometry", Journal of American Society of Mass Spectrometry, 2010, vol. 21, pp. 979-988.

Osaka, Issey et al., "5-Amino-1-naphthol, a novel 1,5-naphthalene derivative matrix suitable for matrix-assisted laser desorption/ionization in-source decay of phosphorylated peptides", Rapid Communications in Mass Spectrometry, 2013, vol. 27, pp. 103-108.

Asakawa, Daiki et al.,"Influence of initial velocity of analytes on in-source decay products in MALDI mass spectrometry using salicylic acid derivative matrices", International Journal of Mass Spectrometry, 2013, vol. 337, pp. 29-33.

Asakawa, Daiki, "Principles of Hydrogen Radical Mediated Peptide/Protein Fragmentation During Matrix-Assisted Laser Desorption/Ionization Mass Spectrometry", Mass Spectrometry Reviews (DOI 10. 1002/mas), 2014, pp. 1-21.

Takayama, Mitsuo, "N—Cα Bond Cleavage of the Peptide Backbone via Hydrogen Abstraction", Journal of American Society for Mass Spectrometry, 2001, vol. 12, pp. 1044-1049.

Demeure, Kevin et al., "Rational Selection of the Optimum MALDI Matrix for Top-Down Proteomics by In-Source Decay", Analytical Chemistry, 2007, vol. 79, No. 22, pp. 8678-8685.

Asakawa, Daiki et al., "Cα—C Bond Cleavage of the Peptide Backbone in MALDI In-Source Decay Using Salicylic Acid Derivative Matrices", Journal of American Society of Mass Spectrometry, 2011, vol. 22, pp. 1224-1233.

Asakawa, Daiki et al., "Matrix Effect on In-Source Decay Products of Peptides in Matrix-Assisted Laser Desorption/Ionization", Mass Spectrometry, 2012, vol. 1, A0002 (9 pages).

* cited by examiner

N-terminus: Acetylation (C2H3O)
C-terminus: Hydroxy (HO)

Singly charged Fragments    Monoisotopic masses    (M+H)+ : 1800.9

| n | a | b | c | d | x | y | z | w | n |
|---|---|---|---|---|---|---|---|---|---|
| 1(D) | 130.1 | 158.0 | 175.1 | 86.1 | 132.0 | 106.1 | 89.0 | 73.0 | 1(S) |
| 2(R) | 286.2 | 314.1 | 331.2 | 201.1 | 295.1 | 269.1 | 252.1 | 160.1 | 2(Y) |
| 3(V) | 385.2 | 413.2 | 430.2 | 371.2 | 394.2 | 368.2 | 351.2 | 337.1 | 3(V) |
| 4(Y) | 548.3 | 576.3 | 593.3 | 456.3 | 507.2 | 481.3 | 464.2 | 422.2 | 4(L) |
| 5(I) | 661.4 | 689.4 | 706.4 | 633.3 | 620.3 | 594.4 | 577.3 | 535.3 | 5(L) |
| 6(H) | 798.4 | 826.4 | 845.4 | 732.4 | 757.4 | 731.4 | 714.4 | 648.4 | 6(H) |
| 7(P) | 895.5 | 923.5 | 940.5 | 869.5 | 904.5 | 878.5 | 861.5 | 785.4 | 7(F) |
| 8(F) | 1042.5 | 1070.5 | 1087.6 | 966.5 | 1001.5 | 975.5 | 958.5 | 932.5 | 8(P) |
| 9(H) | 1179.6 | 1207.6 | 1224.6 | 1113.6 | 1138.6 | 1112.6 | 1095.6 | 1029.5 | 9(H) |
| 10(L) | 1292.7 | 1320.7 | 1337.7 | 1250.6 | 1251.7 | 1225.7 | 1208.6 | 1180.6 | 10(I) |
| 11(L) | 1405.8 | 1433.8 | 1450.8 | 1363.7 | 1414.7 | 1388.7 | 1371.7 | 1279.7 | 11(Y) |
| 12(V) | 1504.8 | 1532.8 | 1549.9 | 1490.8 | 1513.8 | 1487.8 | 1470.8 | 1456.8 | 12(V) |
| 13(Y) | 1667.9 | 1695.9 | 1712.9 | 1575.9 | 1669.9 | 1643.9 | 1626.9 | 1541.8 | 13(R) |
| 14(S) | 1754.9 | 1782.9 | ——— | 1738.9 | ——— | 1758.9 | 1741.9 | 1697.9 | 14(D) |

N-terminus: Hydrogen (H)   C-terminus: Hydroxy (HO)
Singly charged Fragments   Average Masses (M+H)+ : 4330.9

| n | a | b | c | d | x | y | z | w | n |
|---|---|---|---|---|---|---|---|---|---|
| 1(D) | 88.1 | 116.1 | 133.1 | 44.1 | 144.2 | 118.2 | 101.1 | 87.1 | 1(V) |
| 2(A) | 159.2 | 187.2 | 204.2 | — | 243.3 | 217.3 | 200.3 | 186.2 | 2(V) |
| 3(E) | 288.3 | 316.3 | 333.3 | 230.2 | 300.3 | 274.3 | 257.3 | — | 3(G) |
| 4(F) | 435.5 | 463.5 | 480.5 | 359.4 | 357.4 | 331.4 | 314.4 | — | 4(G) |
| 5(R) | 591.6 | 619.7 | 636.7 | 506.5 | 456.5 | 430.5 | 413.5 | 399.5 | 5(V) |
| 6(H) | 728.8 | 756.8 | 773.8 | 662.7 | 587.7 | 561.7 | 544.7 | 484.6 | 6(M) |
| 7(D) | 843.9 | 871.9 | 888.9 | 799.9 | 700.9 | 674.9 | 657.9 | 615.8 | 7(L) |
| 8(S) | 931.0 | 959.0 | 976.0 | 915.0 | 757.9 | 731.9 | 714.9 | — | 8(G) |
| 9(G) | 988.0 | 1016.0 | 1033.0 | — | 871.1 | 845.1 | 828.1 | 800.0 | 9(I) |
| 10(Y) | 1151.2 | 1179.2 | 1196.2 | 1059.1 | 984.3 | 958.3 | 941.2 | 913.2 | 10(I) |
| 11(E) | 1280.3 | 1308.3 | 1325.3 | 1222.3 | 1055.3 | 1029.3 | 1012.3 | — | 11(A) |
| 12(V) | 1379.4 | 1407.4 | 1424.5 | 1365.4 | 1112.4 | 1086.4 | 1069.4 | — | 12(G) |
| 13(H) | 1516.6 | 1544.6 | 1561.6 | 1450.5 | 1240.6 | 1214.6 | 1197.5 | 1140.4 | 13(K) |
| 14(H) | 1653.7 | 1681.7 | 1698.8 | 1587.7 | 1354.7 | 1328.7 | 1311.6 | 1268.6 | 14(N) |
| 15(Q) | 1781.8 | 1809.9 | 1826.9 | 1724.8 | 1441.7 | 1415.7 | 1398.7 | 1382.7 | 15(S) |
| 16(K) | 1910.0 | 1938.0 | 1955.1 | 1852.9 | 1498.8 | 1472.8 | 1455.8 | — | 16(G) |
| 17(L) | 2023.2 | 2051.2 | 2068.2 | 1981.1 | 1597.9 | 1571.9 | 1554.9 | 1540.9 | 17(V) |
| 18(V) | 2122.3 | 2150.3 | 2167.4 | 2108.3 | 1713.0 | 1687.0 | 1670.0 | 1626.0 | 18(D) |
| 19(F) | 2269.5 | 2297.5 | 2314.5 | 2193.4 | 1842.1 | 1816.1 | 1799.1 | 1741.1 | 19(E) |
| 20(F) | 2416.7 | 2444.7 | 2461.7 | 2340.6 | 1913.2 | 1887.2 | 1870.2 | — | 20(A) |
| 21(A) | 2487.7 | 2515.8 | 2532.8 | — | 2060.4 | 2034.4 | 2017.4 | 1941.3 | 21(F) |
| 22(E) | 2616.9 | 2644.9 | 2661.9 | 2558.8 | 2207.6 | 2181.6 | 2164.5 | 2088.4 | 22(F) |
| 23(D) | 2732.0 | 2760.0 | 2777.0 | 2687.9 | 2306.7 | 2280.7 | 2263.7 | 2249.6 | 23(V) |
| 24(V) | 2831.1 | 2859.1 | 2876.1 | 2817.1 | 2419.9 | 2393.9 | 2376.8 | 2334.7 | 24(L) |
| 25(G) | 2888.1 | 2916.1 | 2933.2 | — | 2548.0 | 2522.0 | 2505.0 | 2447.9 | 25(K) |
| 26(S) | 2975.2 | 3003.2 | 3020.3 | 2959.2 | 2676.2 | 2650.2 | 2633.1 | 2576.1 | 26(Q) |
| 27(N) | 3089.3 | 3117.3 | 3134.4 | 3046.3 | 2813.3 | 2787.3 | 2770.3 | 2704.2 | 27(H) |
| 28(K) | 3217.5 | 3245.5 | 3262.5 | 3160.4 | 2950.4 | 2924.4 | 2907.4 | 2841.4 | 28(H) |
| 29(G) | 3274.5 | 3302.6 | 3319.6 | — | 3049.6 | 3023.6 | 3006.6 | 2992.5 | 29(V) |
| 30(A) | 3345.6 | 3373.6 | 3390.7 | — | 3178.7 | 3152.7 | 3135.7 | 3077.6 | 30(E) |
| 31(I) | 3458.8 | 3486.8 | 3503.8 | 3430.7 | 3341.9 | 3315.9 | 3298.8 | 3206.7 | 31(Y) |
| 32(I) | 3571.9 | 3600.0 | 3617.0 | 3543.9 | 3398.9 | 3372.9 | 3355.9 | — | 32(G) |
| 33(G) | 3629.0 | 3657.0 | 3674.0 | — | 3486.0 | 3460.0 | 3443.0 | 3427.0 | 33(S) |
| 34(L) | 3742.2 | 3770.2 | 3787.2 | 3700.1 | 3601.1 | 3575.1 | 3558.1 | 3514.1 | 34(D) |
| 35(M) | 3873.4 | 3901.4 | 3918.4 | 3813.2 | 3738.2 | 3712.2 | 3695.2 | 3629.1 | 35(H) |
| 36(V) | 3972.5 | 4000.5 | 4017.5 | 3958.5 | 3894.4 | 3868.4 | 3851.4 | 3766.3 | 36(R) |
| 37(G) | 4029.5 | 4057.5 | 4074.6 | — | 4041.6 | 4015.6 | 3998.6 | 3922.5 | 37(F) |
| 38(G) | 4086.6 | 4114.6 | 4131.6 | — | 4170.7 | 4144.7 | 4127.7 | 4069.6 | 38(E) |
| 39(V) | 4185.7 | 4213.7 | 4230.8 | 4171.7 | 4241.8 | 4215.8 | 4198.8 | — | 39(A) |
| 40(V) | 4284.9 | 4312.9 | — | 4270.8 | — | 4330.9 | 4313.9 | 4269.8 | 40(D) |

SEQUENCE LISTING

```
<160> NUMBER OF SEQ ID NOS: 2

<210> SEQ ID NO 1
<211> LENGTH: 14
<212> TYPE: PRT
<213> ORGANISM: human
<220> FEATURE:
<221> NAME/KEY: MOD_RES
<222> LOCATION: 1
<223> OTHER INFORMATION: ACETYLATION

<400> SEQUENCE: 1

Asp Arg Val Tyr Ile His Pro Phe His Leu Leu Val Tyr Ser
1               5                   10

<210> SEQ ID NO 2
<211> LENGTH: 40
<212> TYPE: PRT
<213> ORGANISM: human

<400> SEQUENCE: 2

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
                20                  25                  30

Gly Leu Met Val Gly Gly Val Val
                35                  40
```

METHOD FOR SPECIFIC CLEAVAGE OF C ALPHA-C BOND AND SIDE CHAIN OF PROTEIN AND PEPTIDE, AND METHOD FOR DETERMINING AMINO ACID SEQUENCE

BACKGROUND OF THE INVENTION

Technical Field of the Invention

The present invention relates to a method for specific cleavage of a Cα-C bond of a peptide backbone and a side chain of a protein and a peptide. Further, the present invention relates to a method for determining an amino acid sequence of protein and peptide by measuring the protein and the peptide by a mass spectrometry method, in particular MALDI-MS (Matrix-Assisted Laser Desorption/Ionization Mass Spectrometry) using at least one hydroxynitrobenzoic acid selected from the group consisting of 3-hydroxy-2-nitrobenzoic acid, 4-hydroxy-3-nitrobenzoic acid, 5-hydroxy-2-nitrobenzoic acid, 3-hydroxy-5-nitrobenzoic acid and 4-hydroxy-2-nitrobenzoic acid as a matrix.

Background Art

JP-A-2005-326391 (Patent Document 1) and Non-Patent Document 1 disclose that a peptide obtained by previously modifying a peptide with a 2-nitrobenzenesulphenyl group is subjected to MALDI (Matrix-Assisted Laser Desorption/Ionization) mass spectrometry using, as a matrix, α-cyano-3-hydroxycinnamic acid (3-CHCA), 3-hydroxy-4-nitrobenzoic acid (3H4NBA), or a mixture of there. However, these documents neither disclose nor suggest that a Cα-C bond of a peptide backbone and a side chain of protein and peptide are specifically cleaved with such a matrix.

WO 2011/007743 (Patent Document 2) and Non-Patent Document 2 disclose a method for specifically cleaving an N—Cα bond of a peptide backbone by conducting MALDI mass spectrometry using 5-amino salicylic acid (5-ASA) as a matrix.

JP-A-2013-130570 (Patent Document 3) and Non-Patent Document 3 disclose a method for specifically cleaving an N—Cα bond or a Cα-C bond of a peptide backbone including irradiating a protein or a peptide with laser light in the presence of a naphthalene compound substituted with a 1-hydroxy-5-functional group. As the naphthalene compound substituted with a 1-hydroxy-5-functional group, 1-hydroxy-5-aminonaphthalene, or 1,5-dihydroxynaphthalene is used.

Non-Patent Document 4 discloses a method for specifically cleaving a Cα-C bond of a peptide backbone by conducting MALDI mass spectrometry using 5-nitro salicylic acid (5-NSA), 4-nitro salicylic acid (4-NSA), 3-nitro salicylic acid (3-NSA), or 5-formyl salicylic acid (5-FSA).

The In-Source Decay (ISD) method in MALDI mass spectrometry is a method of inducing fragmentation of a sample ion in the ion source, and analyzing the generated fragment ion. For obtaining amino acid sequence information of a peptide chain, it is required that ion species of any one or a plurality of a-, b-, c-, x-, y-, and z-series are continuously detected in the mass spectrometry.

The mainstream in MALDI-ISD in analysis of a peptide and a protein uses a reducing matrix (Non-Patent Document 5). In this case, a hydrogen radical derived from a matrix molecule and induced by laser light irradiation is given to the sample molecule (i.e. reducing matrix) in the condition that the matrix coexists with the sample, and cleavage of an N—Cα bond of a peptide backbone is induced, and mainly, ion species of c-series ion and z-series ion are generated (Non-Patent Document 5, and Non-Patent Document 6). However, when the reducing matrix is used, cleavage on the left side of amino acid proline (Pro, P) is very difficult to occur, and a c-series ion is not generated by cleavage on the left side of proline (Pro, P). Further, when the reducing matrix is used, ion species of d-series ion are hardly generated by cleavage of a side chain.

As a matrix for generating c-series or z-series ion species, for example, 1,5-diaminonaphthalene (1,5-DAN) is known (Non-Patent Document 7). In c-series ion species generated by 1,5-DAN, cleavage on the left side of amino acid proline (Pro, P) is very difficult to occur, and a c-series ion is not generated by cleavage on the left side of proline (Pro, P). This is because proline (Pro, P) has a cyclic structure in the c-series cleavage (including cleavage of N—Cα bond) site. Therefore, it is difficult to obtain sequence information of the site containing proline (Pro, P). Since it is difficult to generate d-series ion species occurring by cleavage of a side chain via a-series ion species, it is not possible to distinguish between leucine (Leu, L) and isoleucine (Ile, I) having completely the same mass of amino acid residue by d-series ion species. In the use of 1,5-DAN, w-series ion species may be generated by cleavage of a side chain via z-series ion species, and in such a case, there is a possibility that leucine (Leu, L) and isoleucine (Ile, I) can be distinguished from each other, but the possibility is limited to the case where there is a basic amino acid such as arginine (Arg, R) or lysin (Lys, K) at the C terminus of the peptide.

Features of the 1,5-DAN matrix that is often used in MALDI-ISD can be summarized as follows:

[1] 1,5-DAN causes generation of c-series, or z-series and/or w-series ion species (generation of a-series and/or d-series ion species is difficult).

[2] 1,5-DAN is suspicious of carcinogenicity.

[3] 1,5-DAN is easy to sublimate in vacuo. Thus, when 1,5-DAN is used, the measuring time is limited, and the quantitative performance is liable to be impaired. Also, carryover, which is contamination with sublimated 1,5-DAN at the time of other measurement, is likely to occur.

[4] 1,5-DAN is easy to deteriorate (be oxidized) in a solution state. For example, 1,5-DAN is easy to deteriorate by oxygen or the like in water or acetonitrile used as a solvent. Thus, it is difficult to stock 1,5-DAN in a solution state.

[5] When 1,5-DAN is used, the surface uniformity of the residue on the sample plate after mixing, dropping and drying of the sample/matrix solution is low, and the thickness largely differs depending on the position on the sample plate. Thus, it is difficult to obtain excellent data by Raster, and the resolving power and the mass accuracy are declined in TOF.

[6] Due to generation of a large quantity of cluster ions derived from the 1,5-DAN matrix, it is difficult to obtain information on the N-terminus side of the peptide chain (normally, several residues on the N-terminus side).

On the other hand, it is also known to use an oxidizing matrix in MALDI-ISD in analysis of peptide and protein (Non-Patent Document 5). In this case, hydrogen radical elimination from the sample molecule occurs in response to laser light irradiation in the condition that the matrix coexists with the sample, and the eliminated hydrogen radical is given to the matrix molecule (i.e. oxidizing matrix) (Non-Patent Document 5). Upon cleavage of a Cα-C bond of a peptide backbone caused by hydrogen radical elimination from the sample molecule, ion species of a-series ion and x-series ion are generated (Non-Patent Documents 5, 8, and 9), and further a d-series ion is easily generated by cleavage of a side chain (Non-Patent Document 5).

As a matrix that promotes hydrogen radical elimination and generates a-series ion species, for example, 5-FSA to which a functional group —CHO is added (Non-Patent Documents 4, 5, and 8), and 5-NSA to which a functional group —$NO_2$ is added (Non-Patent Documents 4, 5, and 8) are known (Non-Patent Documents 4, 5, 8, and 9). However, for general peptides, the generation efficiency of a-series ion species by 5-FSA or 5-NSA tends to be relatively low in comparison with the generation efficiency of c-series ion species by 1,5-DAN.

CITATION LIST

Patent Documents

Patent Document 1: JP-A-2005-326391
Patent Document 2: WO 2011/007743
Patent Document 3: JP-A-2013-130570

Non-Patent Documents

Non-Patent Document 1: "Selective detection of 2-nitrobenzenesulfenyl-labeled peptide by matrix-assisted laser desorption/ionization-time of flight mass spectrometry using a novel matrix", E. Matsuo, C. Toda, M. Watanabe, N. Ojima, S. Izumi, K. Tanaka, S. Tsunasawa, O. Nishimura: Proteomics (2006) Vol. 6, pp. 2042-2049
Non-Patent Document 2: "In-source decay and fragmentation characteristics of peptide using 5-aminosalicylic acid as a matrix in matrix-assisted laser desorption/ionization mass spectrometry", M. Sakakura, M. Takayama: J. Am. Soc. Mass Spectrom. (2010) Vol. 21, pp. 979-988
Non-Patent Document 3: "5-Amino-1-naphthol, a novel 1,5-naphthalene derivative matrix suitable for matrix-assisted laser desorption/ionization in-source decay of phosphorylated peptides", I. Osaka, M. Sakai, M. Takayama: Rapid Commun. Mass Spectrom. (2013) Vol. 27, pp. 103-108
Non-Patent Document 4: "Influence of initial velocity of analytes on in-source decay products in MALDI mass spectrometry using salicylic acid derivative matrices", D. Asakawa, M. Sakakura, M. Takayama: Int. J. Mass spectrom. (2013) Vol. 337, pp. 29-33
Non-Patent Document 5: "Principles of Hydrogen Radical Mediated Peptide/Protein Fragmentation during Matrix-Assisted Laser Desorption/Ionization Mass Spectrometry", D. Asakawa: Mass Spectrometry Reviews (2014) (DOI 10. 1002/mas)
Non-Patent Document 6: "N—Cα bond cleavage of the peptide backbone via hydrogen abstraction", M. Takayama: J. Am. Soc. Mass Spectrom. (2001) Vol. 12, pp. 1044-1049
Non-Patent Document 7: "Rational selection of the optimum MALDI matrix for top-down proteomics by in-source decay", K. Demeure, L. Quinton, V. Gabelica, E.-D. Pauw: Anal. Chem. (2007) Vol. 79, pp. 8678-8685
Non-Patent Document 8: "Cα-C Bond Cleavage of the Peptide Backbone in MALDI In-Source Decay Using Salicylic Acid Derivative Matrices", D. Asakawa, M. Takayama: J. Am. Soc. Mass Spectrom. (2011) Vol. 22, pp. 1224-1233
Non-Patent Document 9: "Matrix Effect on In-Source Decay Products of Peptides in Matrix-Assisted Laser Desorption/Ionization", D. Asakawa, M. Sakakura, M. Takayama, Mass Spectrometry (2012) Vol. 1, A0002

SUMMARY OF THE INVENTION

Problems to be Solved by the Invention

As described above, in mass spectrometry of peptide or protein, c-series ion species can be obtained with high generation efficiency and high sensitivity by using 1,5-DAN; however, for a-series or x-series ion species, there is currently no oxidizing matrix capable of generating a-series or x-series ion species with adequately high generation efficiency and sensitivity as well as with small contamination of other ion species. Also, currently, it is not possible to distinguish between leucine (Leu, L) and isoleucine (Ile, I) which are amino acids having the same mass by the matrix for generating c-series or z-series ion species. In such a current state, there is a demand for a method for specifically cleaving a Cα-C bond of protein or peptide efficiently, detecting ion species such as a-series ion with high sensitivity with small contamination of other ion species, and achieving rapid analysis. Further, there is a demand for a method for specifically cleaving a side chain, detecting d-series ion with high sensitivity, and thereby determining amino acid sequences of protein and peptide.

An object of the present invention is to provide a method for specifically cleaving a Cα-C bond of a peptide backbone and/or a side chain of a protein and a peptide, and a method for determining amino acid sequences of protein and peptide by the method.

Means for Solving the Problems

The present inventors have intensively studied, and as a result, have found that the above object can be achieved by using, as a matrix, at least one hydroxynitrobenzoic acid selected from the group consisting of 3-hydroxy-2-nitrobenzoic acid, 4-hydroxy-3-nitrobenzoic acid, 5-hydroxy-2-nitrobenzoic acid, 3-hydroxy-5-nitrobenzoic acid and 4-hydroxy-2-nitrobenzoic acid.

The present invention includes the following.

(1) A method for specifically cleaving a Cα-C bond of a peptide backbone and/or a side chain bond of a protein or a peptide, comprising irradiating a protein or a peptide with laser light in the presence of at least one hydroxynitrobenzoic acid selected from the group consisting of:
3-hydroxy-2-nitrobenzoic acid:

[Chemical formula 1]

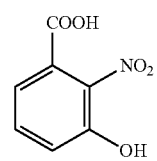

4-hydroxy-3-nitrobenzoic acid:

[Chemical formula 2]

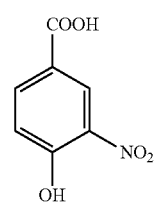

5-hydroxy-2-nitrobenzoic acid:

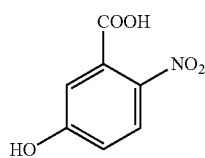

3-hydroxy-5-nitrobenzoic acid:

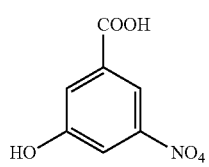

and
4-hydroxy-2-nitrobenzoic acid:

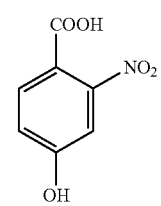

(2) A method for determining an amino acid sequence of a protein or a peptide, comprising:
irradiating a protein or a peptide with laser light in the presence of at least one hydroxynitrobenzoic acid selected from the group consisting of:
3-hydroxy-2-nitrobenzoic acid:

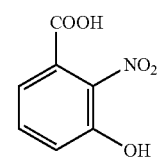

4-hydroxy-3-nitrobenzoic acid:

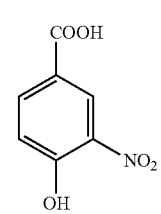

5-hydroxy-2-nitrobenzoic acid:

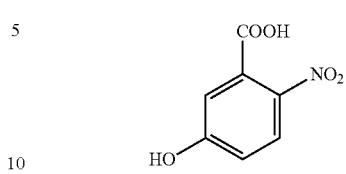

3-hydroxy-5-nitrobenzoic acid:

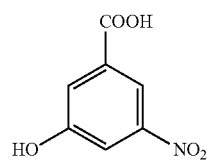

and
4-hydroxy-2-nitrobenzoic acid:

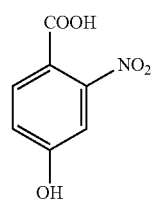

to specifically cleave a Cα-C bond of a peptide backbone and/or a side chain bond; and
analyzing generated fragment ions by mass spectrometry.

(3) A method for determining an amino acid sequence of a protein or a peptide, comprising:
irradiating a protein or a peptide with laser light in the presence of at least one hydroxynitrobenzoic acid selected from the group consisting of 3-hydroxy-2-nitrobenzoic acid, 4-hydroxy-3-nitrobenzoic acid, 5-hydroxy-2-nitrobenzoic acid, 3-hydroxy-5-nitrobenzoic acid, and 4-hydroxy-2-nitrobenzoic acid as a matrix to specifically cleave a Cα-C bond of a peptide backbone and/or a side chain bond; and
analyzing generated fragment ions by MALDI mass spectrometry.

(4) The method for determining an amino acid sequence of a protein or a peptide according to the above (2) or (3), wherein as the generated fragment ions, a-series ion species and/or x-series ion species are analyzed.

(5) The method for determining an amino acid sequence of a protein or a peptide according to the above (2) or (3), wherein as the generated fragment ions, a-series ion species and d-series ion species are analyzed.

(6) A reagent for specifically cleaving a Cα-C bond of a peptide backbone and/or a side chain bond of a protein or a peptide, comprising at least one hydroxynitrobenzoic acid selected from the group consisting of:

3-hydroxy-2-nitrobenzoic acid:

[Chemical formula 11]

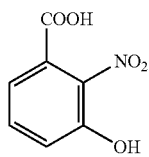

4-hydroxy-3-nitrobenzoic acid:

[Chemical formula 12]

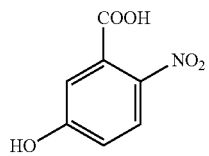

5-hydroxy-2-nitrobenzoic acid:

[Chemical formula 13]

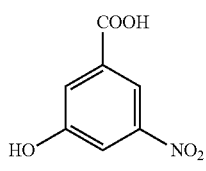

3-hydroxy-5-nitrobenzoic acid:

[Chemical formula 14]

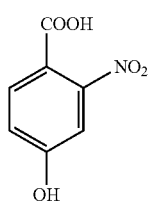

and
4-hydroxy-2-nitrobenzoic acid:

[Chemical formula 15]

In the present invention, in MALDI-ISD analysis, ISD fragmentation is promoted generally by setting the laser intensity higher than that in a normal analysis. That is, in the present invention, by irradiating a protein or a peptide of a sample to be analyzed with laser light having an intensity somewhat higher than the quantity and density required for generation of proton addition molecule [M+H]$^+$ derived from the sample in the presence of at least one hydroxynitrobenzoic acid selected from the group consisting of 3-hydroxy-2-nitrobenzoic acid, 4-hydroxy-3-nitrobenzoic acid, 5-hydroxy-2-nitrobenzoic acid, 3-hydroxy-5-nitrobenzoic acid and 4-hydroxy-2-nitrobenzoic acid as a matrix, hydrogen radical elimination reaction from the protein or the peptide is promoted to cause generation of mainly a-series and/or x-series ion species, and further cause generation of d-series ion species.

Advantageous Effect of the Invention

In the present invention, by irradiating a protein or a peptide with laser light in the presence of at least one hydroxynitrobenzoic acid selected from the group consisting of 3-hydroxy-2-nitrobenzoic acid, 4-hydroxy-3-nitrobenzoic acid, 5-hydroxy-2-nitrobenzoic acid, 3-hydroxy-5-nitrobenzoic acid and 4-hydroxy-2-nitrobenzoic acid, hydrogen radical elimination reaction from the protein or the peptide is promoted, and a Cα-C bond of a peptide backbone and/or a side chain bond can be specifically cleaved.

As a result of specific cleavage of a Cα-C bond of a peptide backbone and/or a side chain bond, a-series and/or x-series ion species are mainly generated as fragment ions, and further d-series ion species are also generated. By detecting and analyzing the a-series and/or the x-series ion species by mass spectrometry, it is possible to detect cleavage on the left side of proline (Pro, P) and to obtain sequence information of a site containing proline (Pro, P). Meanwhile, by detecting and analyzing the d-series ion species by mass spectrometry, it is possible to distinguish between leucine (Leu, L) and isoleucine (Ile, I) having completely the same mass of amino acid residue. As described above, according to the present invention, it is possible to obtain more amino acid sequence information rapidly with high sensitivity, and with high coverage for a protein or a peptide to be analyzed. In particular, it is possible to obtain amino acid sequence information by only one MS measurement without conducting a multistage analysis as in MS/MS.

Figure 1:
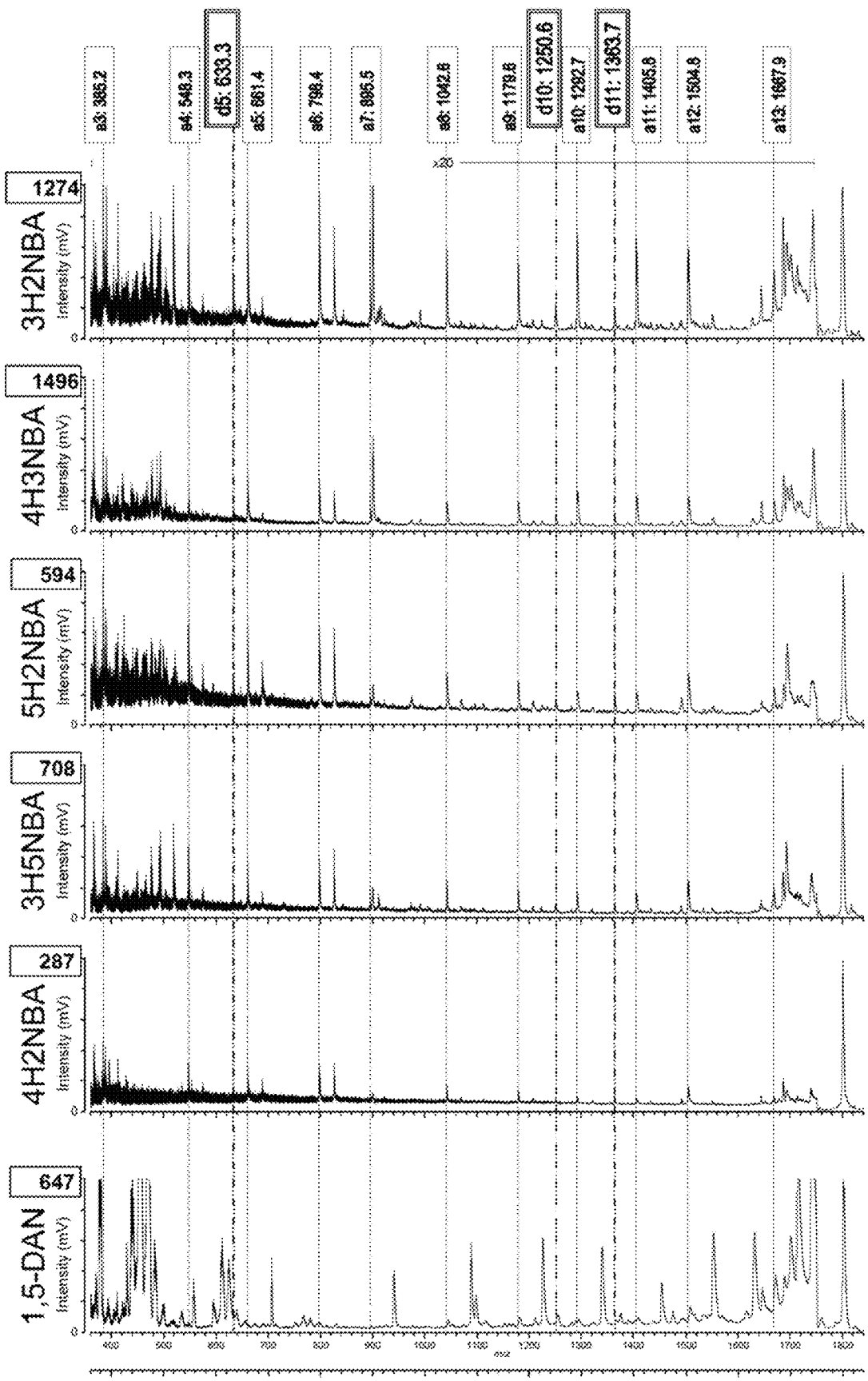
FIG. 1 shows overall views of ISD mass spectra of N-Acetyl-Renin substrate when 3-hydroxy-2-nitrobenzoic acid (3H2NBA), 4-hydroxy-3-nitrobenzoic acid (4H3NBA), 5-hydroxy-2-nitrobenzoic acid (5H2NBA), 3-hydroxy-5-nitrobenzoic acid (3H5NBA), 4-hydroxy-2-nitrobenzoic acid (4H2NBA) and 1,5-diaminonaphthalene (1,5-DAN) are used as a matrix from the top. The horizontal axis represents mass/charge (m/z), and the vertical axis represents ion intensity.

(A) 3-hydroxy-2-nitrobenzoic acid (3H2NBA),
(B) 4-hydroxy-3-nitrobenzoic acid (4H3NBA),
(C) 5-hydroxy-2-nitrobenzoic acid (5H2NBA),
(D) 3-hydroxy-5-nitrobenzoic acid (3H5NBA),
(E) 4-hydroxy-2-nitrobenzoic acid (4H2NBA),
(F) 5-nitrosalicylic acid (5-NSA), or
(G) 1,5-diaminonaphthalene (1,5-DAN)
as a matrix, and drying the mixed solution.

MODES FOR CARRYING OUT OF THE INVENTION

For obtaining amino acid sequence information of peptide chains for a protein or a peptide to be analyzed, it is a requirement that ion species of any one or a plurality of a-, b-, c-, x-, y-, and z-series are detected continuously in mass spectrometry. The following chemical structural formula shows the naming rule of fragmentation of a peptide backbone for a peptide composed of four residues as an example. $R_1$, $R_2$, $R_3$, and $R_4$ each represent a side chain of an amino acid residue.

[Chemical formula 16]

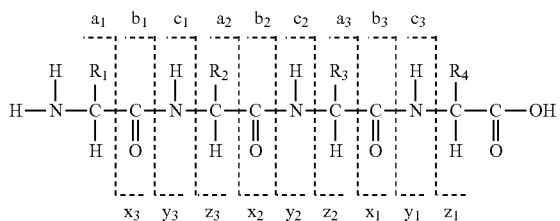

Next, referring to chemical schemes, generation mechanisms of c-series ion and z-series ion, and, a-series ion and x-series ion by cleavage of a peptide backbone will be described (see scheme 1 of Hon-Patent document 8).

[Chemical formula 17]

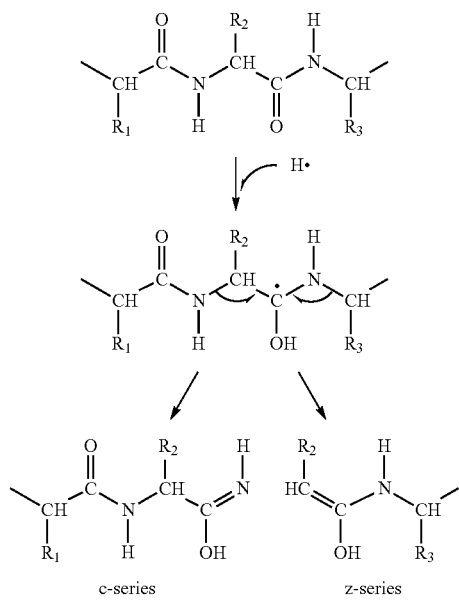

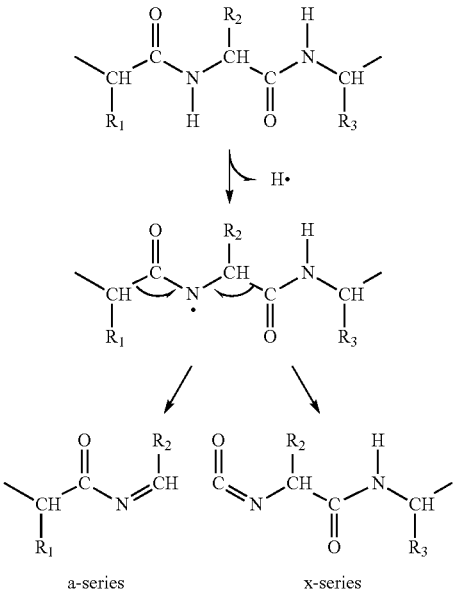

The scheme (a) shows a mechanism of generation of c-series ion and z-series ion by cleavage of an N—Cα bond of a peptide backbone. When laser light irradiation is conducted in the condition that a reducing matrix coexists with a protein or peptide sample, a hydrogen radical derived from the matrix molecule and induced by the laser light irradiation is given to the sample molecule (i.e. reducing matrix), and cleavage of an N—Cα bond of the peptide backbone is induced, and mainly, ion species of c-series ion and/or z-series ion are generated. Since proline (Pro, P) has a cyclic structure in the c-series cleavage (including cleavage of N—Cα bond) site, cleavage of an N—Cα bond is very difficult to occur in the case of proline (Pro, P), and a c-series ion is not generated by cleavage on the left side of proline (Pro, P).

The scheme (b) shows a mechanism of generation of a-series ion and x-series ion by cleavage of a Cα-C bond of a peptide backbone. When laser light irradiation is conducted in the condition that an oxidizing matrix coexists with a protein or peptide sample, hydrogen radical elimination from the sample molecule occurs by the laser light irradiation, and the eliminated hydrogen radical is given to the matrix molecule (oxidizing matrix). Upon cleavage of a Cα-C bond of the peptide backbone caused by hydrogen radical elimination from the sample molecule, ion species of a-series ion and/or x-series ion are generated. Further, d-series ion species are easily generated by cleavage of a side chain from the a-series ion species.

[Matrix]

In the present invention, a protein or peptide sample is irradiated with laser light in the presence of at least one hydroxynitrobenzoic acid selected from the group consisting of 3-hydroxy-2-nitrobenzoic acid, 4-hydroxy-3-nitrobenzoic acid, 5-hydroxy-2-nitrobenzoic acid, 3-hydroxy-5-nitrobenzoic acid and 4-hydroxy-2-nitrobenzoic acid as a matrix. As the specific hydroxynitrobenzoic acid, only one kind or a combination of two or more kinds may be used. According to the above scheme (b), a Cα-C bond of a peptide backbone and/or a side chain bond are/is specifically cleaved. Hereinafter, more specific chemical schemes are shown while taking 3-hydroxy-2-nitrobenzoic acid (3H2NBA) as an example.

[Chemical formula 18]

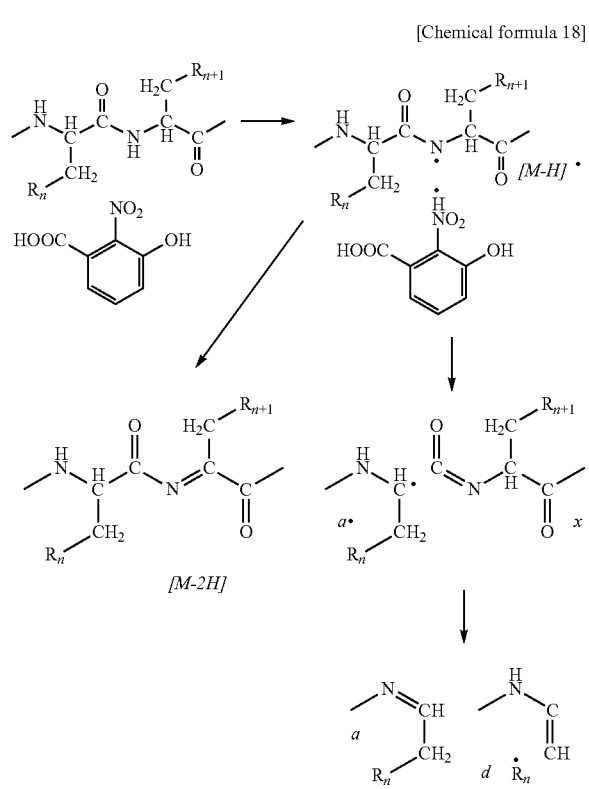

When a protein or peptide sample is irradiated with laser light in the presence of at least one hydroxynitrobenzoic acid selected from the group consisting of 3-hydroxy-2-nitrobenzoic acid, 4-hydroxy-3-nitrobenzoic acid, 5-hydroxy-2-nitrobenzoic acid, 3-hydroxy-5-nitrobenzoic acid and 4-hydroxy-2-nitrobenzoic acid as a matrix, hydrogen radical elimination from the sample molecule occurs by the laser light irradiation, and the eliminated hydrogen radical is given to the specific hydroxynitrobenzoic acid molecule described above. The specific hydroxynitrobenzoic acid has a high acceptability of hydrogen radical by a nitro group, and hydrogen radical elimination from the sample molecule easily occurs. Upon cleavage of a Cα-C bond of a peptide backbone caused by the hydrogen radical elimination from the sample molecule, ion species of a-series ion and/or x-series ion are generated. Further, ion species of d-series ion are easily generated by cleavage of a side chain from the a-series ion species.

The generated ion species of a-series ion and/or x-series ion, and the ion species of d-series ion generated by cleavage of a side chain are subjected to mass spectrometry, and the amino acid sequence of the protein or the peptide can be determined.

[Preparation of Crystal, for Mass Spectrometry]

A crystal for mass spectrometry can be obtained through the step of forming, on a target plate for mass spectrometry, a liquid droplet of a mixture liquid containing, in a solvent, at least a protein or a peptide to be analyzed, and at least one hydroxynitrobenzoic acid matrix selected from the group consisting of 3-hydroxy-2-nitrobenzoic acid, 4-hydroxy-3-nitrobenzoic acid, 5-hydroxy-2-nitrobenzoic acid, 3-hydroxy-5-nitrobenzoic acid and 4-hydroxy-2-nitrobenzoic acid, and the step of removing the solvent from the formed liquid droplet of the mixture liquid to obtain a non-volatile matter (i.e., at least the analyte and the matrix) contained in the mixture liquid as a residue. The thus obtained residue is a crystal for mass spectrometry. In this specification, the term "crystal for mass spectrometry" is synonymous with the term "residue".

As the target for mass spectrometry, a conductive metal plate usually used in MALDI mass spectrometry may be used. Specifically, a stainless plate may be used.

A specific method for preparing the liquid droplet of the mixture liquid on the target plate is not particularly limited. For example, first, a sample solution containing an analyte, and a matrix solution are prepared separately from each other. Then, these solutions are mixed to obtain a mixture liquid, and the obtained mixture liquid is dropped onto a target plate. Alternatively, these solutions may be mixed on a target plate by dropping these solutions onto the same position on the target plate (on-target mix). In the case of on-target mix, the order of dropping the solutions is not particularly limited.

The solvent of the mixture liquid may be selected from the group consisting of water, acetonitrile (ACN), trifluoroacetic acid (TFA), methanol (MeOH), ethanol (EtOH), tetrahydrofuran (THF), dimethylsulfoxide (DMSO), and the like. More specifically, as the solvent of the mixture liquid, an aqueous ACN solution, an aqueous ACN-TFA solution, MeOH-TFA, an aqueous MeOH solution, an aqueous EtOH-TFA solution, an aqueous EtOH solution, an aqueous THF-TFA solution, an aqueous THF solution, an aqueous DMSO-TFA solution, an aqueous DMSO solution or the like is used, and more preferably, an aqueous ACN solution or an aqueous ACN-TFA solution may be used. The concentration of ACN in the aqueous ACN-TFA solution may be, for example, 10 to 90 vol %, preferably 25 to 75 vol %, and the concentration of TEA in the aqueous ACN-TFA solution may be, for example, 0.05 to 1 vol %, preferably 0.05 to 0.1 vol %.

The volume of the liquid droplet of the mixture liquid is not particularly limited, and may be appropriately determined by those skilled in the art. When a well is provided on the target plate, the liquid droplet of the mixture liquid may be formed in the well. In this case, the liquid droplet is formed so as to have a volume that can be held in the well. More specifically, the liquid droplet may be formed so as to have a volume of about 0.1 µL to 2 µL, for example, about 0.5 µL.

Next, the solvent is removed from the liquid droplet of the mixture liquid on the target plate. The removal of the solvent includes natural evaporation of the solvent. The amount of the matrix contained per one residue (that is, per one crystal for mass spectrometry) generated by evaporation may be, for example, 1 pmol to 1,000 nmol, preferably 10 pmol to 100 nmol as a guide. The amount of the analyte may be in the range of, for example, 1 amol to 100 pmol, or in the range of 100 amol to 50 pmol of sample with respect to 10 nmol of the matrix.

The residue has a substantially circular shape on a surface in contact with the target plate. That is, the outer edge of the residue is substantially circular. The average diameter of the substantially circular shape may vary depending on the amount of the sample, the volume of the liquid droplet, the amount of the matrix, the composition of the solvent etc., but is for example 0.1 to 3 mm, preferably 0.5 to 2 mm. It is to be noted that the average diameter is the average of the lengths of line segments cut from lines passing through the center of gravity of the substantially circular shape by the outer edge of the residue.

When an ordinary metallic plate is used as the target for mass spectrometry, the substance to be analyzed mainly exists in the substantial circle in the substantially circular residue obtained by removal of the solvent. Therefore, it is possible to easily conduct ionization of the substance to be analyzed without specifying the laser irradiation position at the time of ionization.

[Mass Spectrometer]

A mass spectrometer used in the present invention is not particularly limited as long as it is used in combination with a MALDI (Matrix-Assisted Laser Desorption/Ionization) ion source. Examples of such a mass spectrometer include MALDI-TOF (Matrix-Assisted Laser Desorption/Ionization-Time-of-Flight) mass spectrometers, MALDI-QIT (Matrix-Assisted Laser Desorption/Ionization-Quadrupole Ion Trap) mass spectrometers, MALDI-QIT-TOF (Matrix-Assisted Laser Desorption/Ionization-Quadrupole Ion Trap-Time-of-Flight) mass spectrometers, MALDI-Q-TOF (Matrix-Assisted Laser Desorption/Ionization-Quadrupole-Time-of-Flight) mass spectrometers, MALDI-FTICR (Matrix-Assisted Laser Desorption/Ionization-Fourier Transform Ion Cyclotron Resonance) mass spectrometers, and MALDI-Orbitrap (Matrix-Assisted Laser Desorption/Ionization-Orbitrap) mass spectrometers.

EXAMPLES

Hereinbelow, the present invention will be described specifically with reference to examples, but is not limited to the following examples.

In the following examples, the following two kinds of peptide samples were used.

N-Acetyl-Renin Substrate (amino acid sequence: Ac-DRVYIHPFHLLVYS) (SEQ ID NO: 1)

Amyloid β [1-40] (amino acid sequence: DAEFRHDS-GYEVHHQKLVFFAEDVGSNKGAIIGLMVGGVV) (SEQ ID NO: 2)

As a matrix, the following seven kinds were used.
3H2NBA (3-hydroxy-2-nitrobenzoic acid), present invention

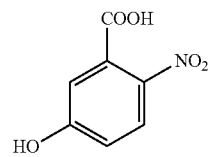

[Chemical formula 19]

4H3NBA (4-hydroxy-3-nitrobenzoic acid), present invention

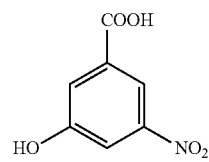

[Chemical formula 20]

5H2NBA (5-hydroxy-2-nitrobenzoic acid), present invention

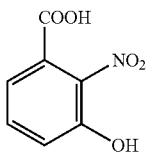

[Chemical formula 21]

3H5NBA (3-hydroxy-5-nitrobenzoic acid), present invention

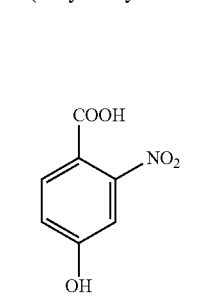

[Chemical formula 22]

4H2NBA (4-hydroxy-2-nitrobenzoic acid), present invention

5-NSA (5-nitrosalicylic acid), for comparison

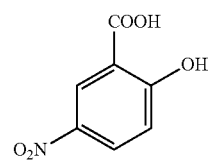

[Chemical formula 23]

1,5-DAN (1,5-Diaminonaphthalene), for comparison

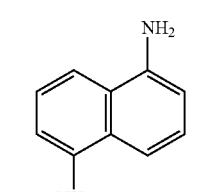

[Chemical formula 24]

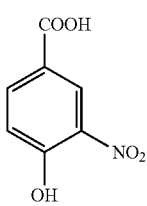

[Chemical formula 25]

Among the above matrixes, 3H2NBA, 4H3NBA, 5H2NBA, 3H5NBA, 4H2NBA and 5-NSA have a functional group —$NO_2$. This —$NO_2$ group exerts the effect of drawing out a hydrogen radical from the peptide sample by laser light irradiation, and causes cleavage of a Cα-C bond of a peptide backbone. As a result, a-series ion species and x-series ion species are generated, and further d-series ion species are generated.

Among the above matrixes, 1,5-DAN has a functional group —NH$_2$. The —NH$_2$ group exerts the effect of generating a hydrogen radical derived from the 1,5-DAN molecule by laser light irradiation, and adding the hydrogen radical to the peptide sample, and causes cleavage of an N—Cα bond of a peptide backbone. As a result, c-series ion species and z-series ion species are generated.

Sample plate: a stainless plate having a thickness of 2 mm was used.

Mass spectrometer: MALDI-Time-of-Flight mass spectrometer [AXIMA-Performance (registered trademark), available from Shimadzu Corporation] was used.

Example 1

Peptide Sample: N-Acetyl-Renin Substrate (Ac-DRVY-IHPFHLLVYS) (SEQ ID NO: 1)
Matrix:
3H2NBA (3-hydroxy-2-nitrobenzoic acid), present invention
4H3NBA (4-hydroxy-3-nitrobenzoic acid), present invention
5H2NBA (5-hydroxy-2-nitrobenzoic acid), present invention
3H5NBA (3-hydroxy-5-nitrobenzoic acid), present invention
4H2NBA (4-hydroxy-2-nitrobenzoic acid), present invention
1,5-DAN (1,5-Diaminonaphthalene), for comparison
[Operation]

(1) As a peptide sample solution, a 20 pmol/μL N-Acetyl-Renin Substrate solution in water was prepared.

(2) As a matrix solution, a 10 mg/mL solution of 3H2NBA, 4H3NBA, 5H2NBA, 3H5NBA, or 4H2NBA in 75% ACM, water was prepared, and for comparison, a 10 mg/mL solution of 1,5-DAN in 75% ACN, water was prepared.

(3) The sample solution (0.5 μL) prepared in (1) was dropped onto a MALDI sample plate, and then the matrix solution (0.5 μL) prepared in (2) was dropped thereonto (on-target mix). The amount of the peptide sample per one well was 10 pmol.

(4) After the solvent was volatilized, measurement was conducted by a Raster analysis for 40×40=1,600 points in a 1.2 mm- to 1.7 mm-square depending on the extent of the residue on the plate by MALDI TOFMS [AXIMA Performance (registered trademark), available from Shimadzu Corporation)] in a positive ion mode and linear mode.
[Results]

Figure 2:
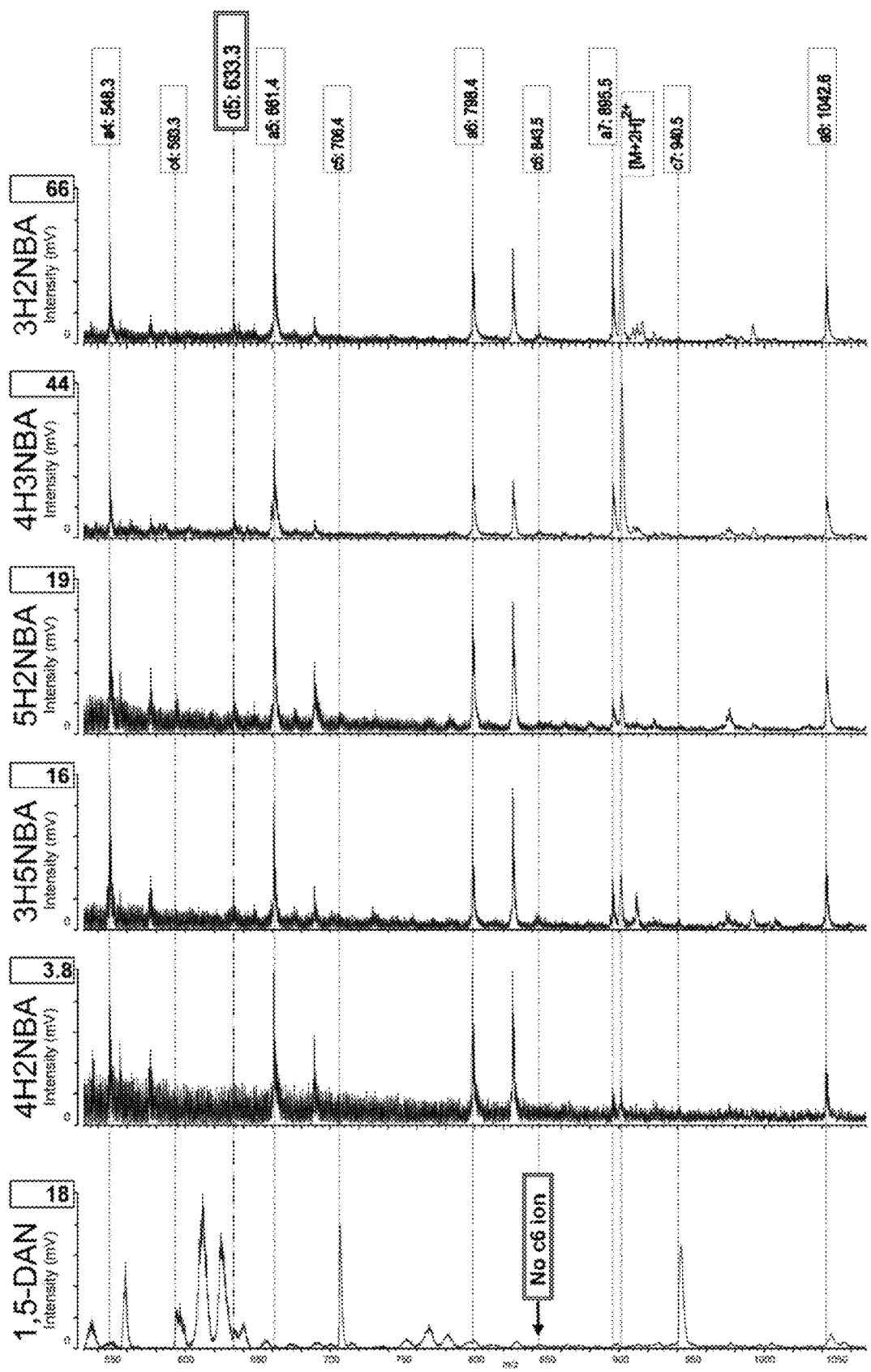
FIG. 2 is a partial enlarged view of a low mass region in FIG. 1.
Figure 3:
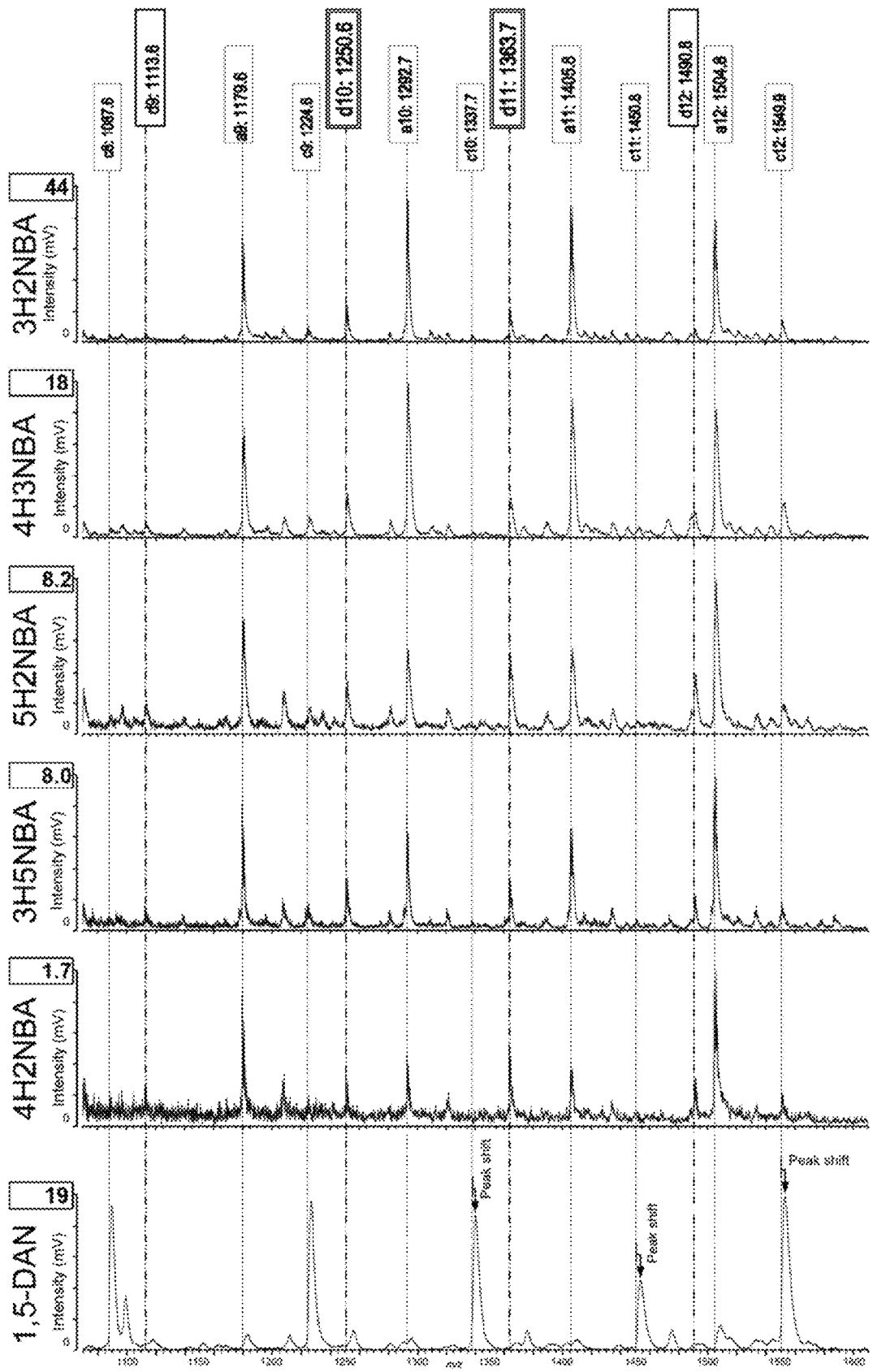
FIG. 3 is a partial enlarged view of a high mass region in FIG. 1.

FIG. 1 shows overall views of ISD mass spectra (m/z: 360-1840) of N-Acetyl-Renin substrate when 3H2NBA (top row), 4H3NBA (second row), 5H2NBA (third row), 3H5NBA (fourth row), 4H2NBA (fifth row), or 1,5-DAN (bottom row) is used as a matrix, FIG. 2 is a partial enlarged view of a low mass region in FIG. 1 (m/z: 530-1070), and FIG. 3 is a partial enlarged view of a high mass region in FIG. 1 (m/z: 1030-1620).

As shown in the spectra of the bottom rows in FIGS. 1 and 2, when 1,5-DAN was used, a large variety and a large quantity of cluster ions derived from the matrix were detected in the low mass region (for example, in FIG. 2, a large number of high intensity peaks observed in m/z: 420 to 650). Therefore, even if c-series ion species are detected, analysis tends to be difficult. Also as shown in the spectrum, of the bottom row in FIG. 2, a c6 ion was not detected. This is because the seventh amino acid from the N-terminus of N-Acetyl-Renin Substrate (amino acid sequence: Ac-DRVYIH"P"FHLLVYS) is proline (Pro, P), and a c-series ion between the previous sixth amino acid histidine (His, H) and the seventh amino acid was not detected.

In contrast, as shown in the spectra of the first to the fifth rows in FIGS. 1 and 2, a-series ion species including an a6 ion were continuously detected without being buried in Cluster ions when 3H2NBA, 4H3NBA, 5H2NBA, 3H5NBA, or 4H2NBA was used.

As shown in the spectrum of the bottom row in FIG. 3, when 1,5-DAN was used, all the c-series ion species were detected in the high mass region; however, the mass resolution was low and the mass accuracy was also low. This is mainly attributable to the fact that the form of the residue after dropping the 1,5-DAN solution and the sample solution on the sample plate and drying the mixed solution is nonuniform (see, for example, the later-described FIG. 9(G)), and the thickness differs depending on the site due to growth of needle-like giant crystals, and thus the mass resolution and the mass accuracy deteriorate in the Time-of-Flight mass spectrometry. Accordingly, it is expected to be difficult to distinguish between amino acids [for example, Ile/Leu (113)←→Asn (114)←→Asp (115), Gln/Lys (128) ←→Glu (129)] having a difference in mass of 1, for example.

In contrast, as mainly shown in FIGS. 1, 2 and 3, when 3H2NBA, 4H3NBA, 5H2NBA, 3H5NBA, or 4H2NBA was used, not only all the a-series ion species were detected, but also d5, d10, and d11 were detected. Therefore, it could be determined that the fifth amino acid from the N-terminus of N-Acetyl-Renin Substrate (amino acid sequence: Ac-DRVY"I"HPFH"LL"VYS) is isoleucine (Ile, I), and both the tenth and eleventh amino acids are leucine (Leu, L). In other words, it could be determined that the fifth amino acid from the N-terminus is not leucine (Leu, L) having the same mass number, but is isoleucine (Ile, I), and the tenth and the eleventh amino acids are not isoleucine (Ile, I), but are leucine (Leu, L).

Figure 4:
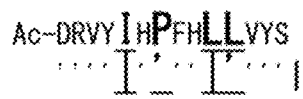
FIG. 4 is an ISD ion theoretical value list of N-Acetyl-Renin substrate.

FIG. 4 shows an ISD ion theoretical value list of N-Acetyl-Renin substrate.

Example 2

Peptide sample: Amyloid β [1-40] (amino acid sequence: DAEFRHDSGYEVHHQKLYFFAEDVGSMKGAIIGLM-VGGW) (SEQ ID NO: 2)
Matrix:
3H2NBA (3-hydroxy-2-nitrobenzoic acid), present invention
4H3NBA (4-hydroxy-3-nitrobenzoic acid), present invention
5H2NBA (5-hydroxy-2-nitrobenzoic acid), present invention
3H5NBA (3-hydroxy-5-nitrobenzoic acid), present invention
4H2NBA (4-hydroxy-2-nitrobenzoic acid), present invention
5-NSA (5-nitrosalicylic acid), for comparison
[Operation]

(1) As a peptide sample solution, a 20 pmol/μL Amyloid β [1-40] solution in 50% ACM 0.1% TEA water was prepared.

(2) As a matrix solution, a 10 mg/mL solution of 3H2NBA, 4H3NBA, 5H2NBA, 3H5NBA, or 4H2NBA in 75% ACN, water was prepared, and for comparison, a 10 mg/mL solution of 5-NSA in 75% ACN, water was prepared.

(3) The sample solution (0.5 μL) prepared in (1) was dropped onto a MALDI sample plate, and then the matrix solution (0.5 µL) prepared in (2) was dropped thereon to (on-target mix). The amount of the peptide sample per one well was 10 pmol.

(4) After the solvent was volatilized, measurement was conducted by a Raster analysis for 40×40=1,600 points in a 1.2 mm- to 1.7 mm-square depending on the extent of the residue on the plate by MALDI TOFMS [AXIMA Performance (registered trademark), available from Shimadzu Corporation)] in a positive ion mode and linear mode.

[Results]

Figure 5:
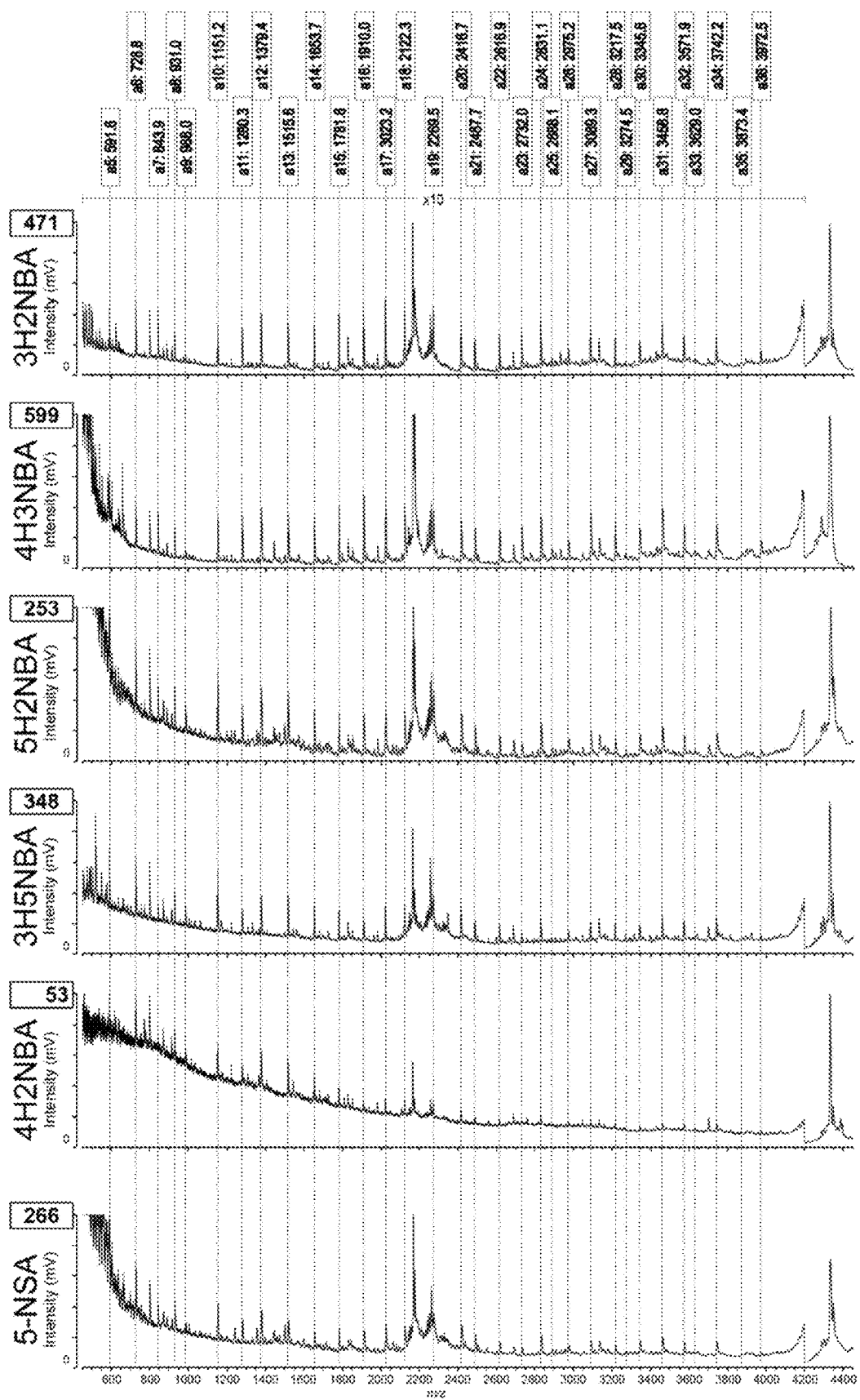
FIG. 5 is overall views of ISD mass spectra of Amyloid β [1-40] when 3-hydroxy-2-nitrobenzoic acid (3H2NBA), 4-hydroxy-3-nitrobenzoic acid (4H3NBA), 5-hydroxy-2-nitrobenzoic acid (5H2NBA), 3-hydroxy-5-nitrobenzoic acid (3H5NBA), 4-hydroxy-2-nitrobenzoic acid (4H2NBA) and 5-nitro salicylic acid (5-NSA) are used as a matrix from the top. The horizontal axis represents mass/charge (n/z), and the vertical axis represents ion intensity.
Figure 6:
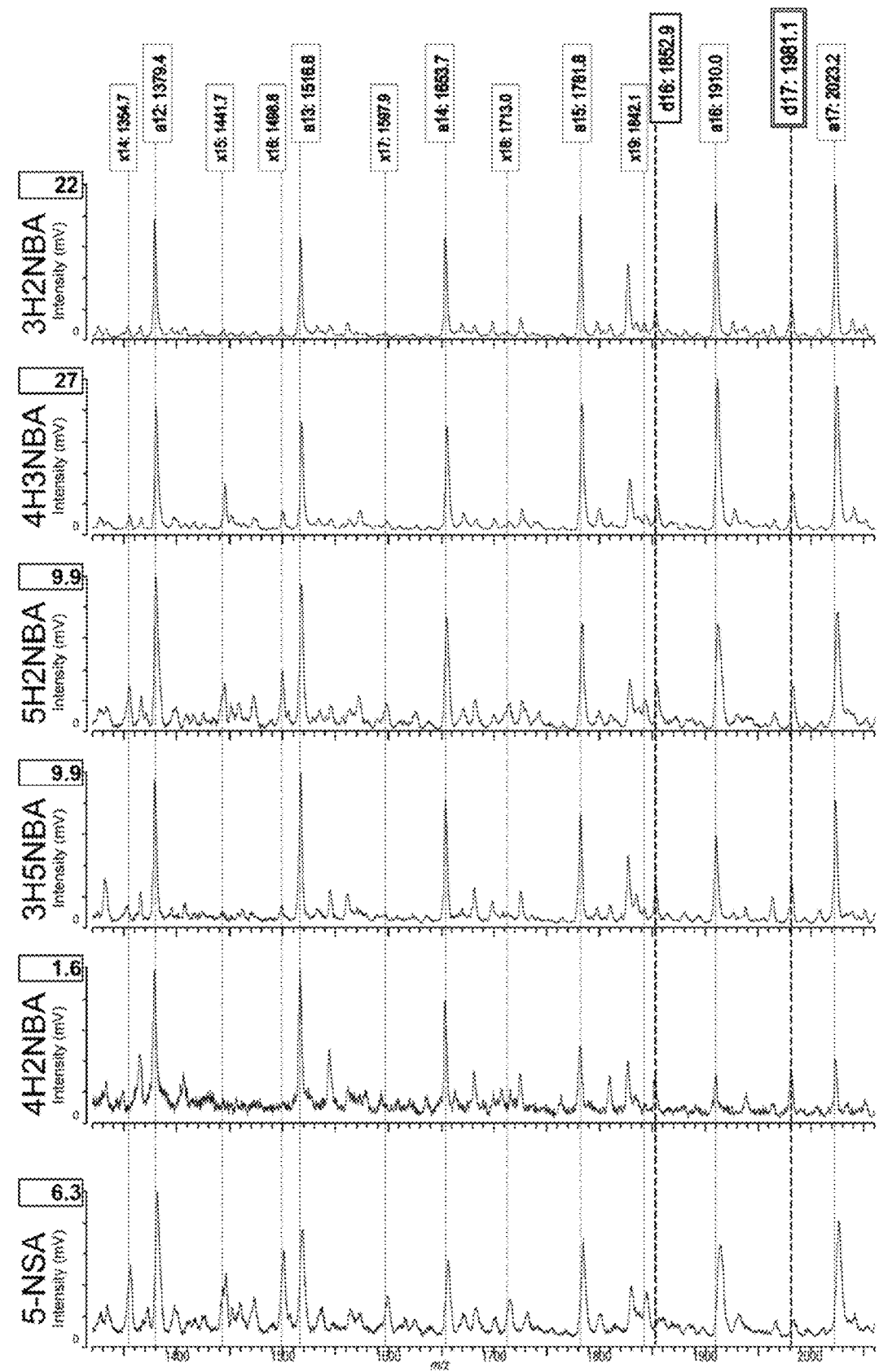
FIG. 6 is a partial enlarged view of a low mass region in FIG. 5.
Figure 7:
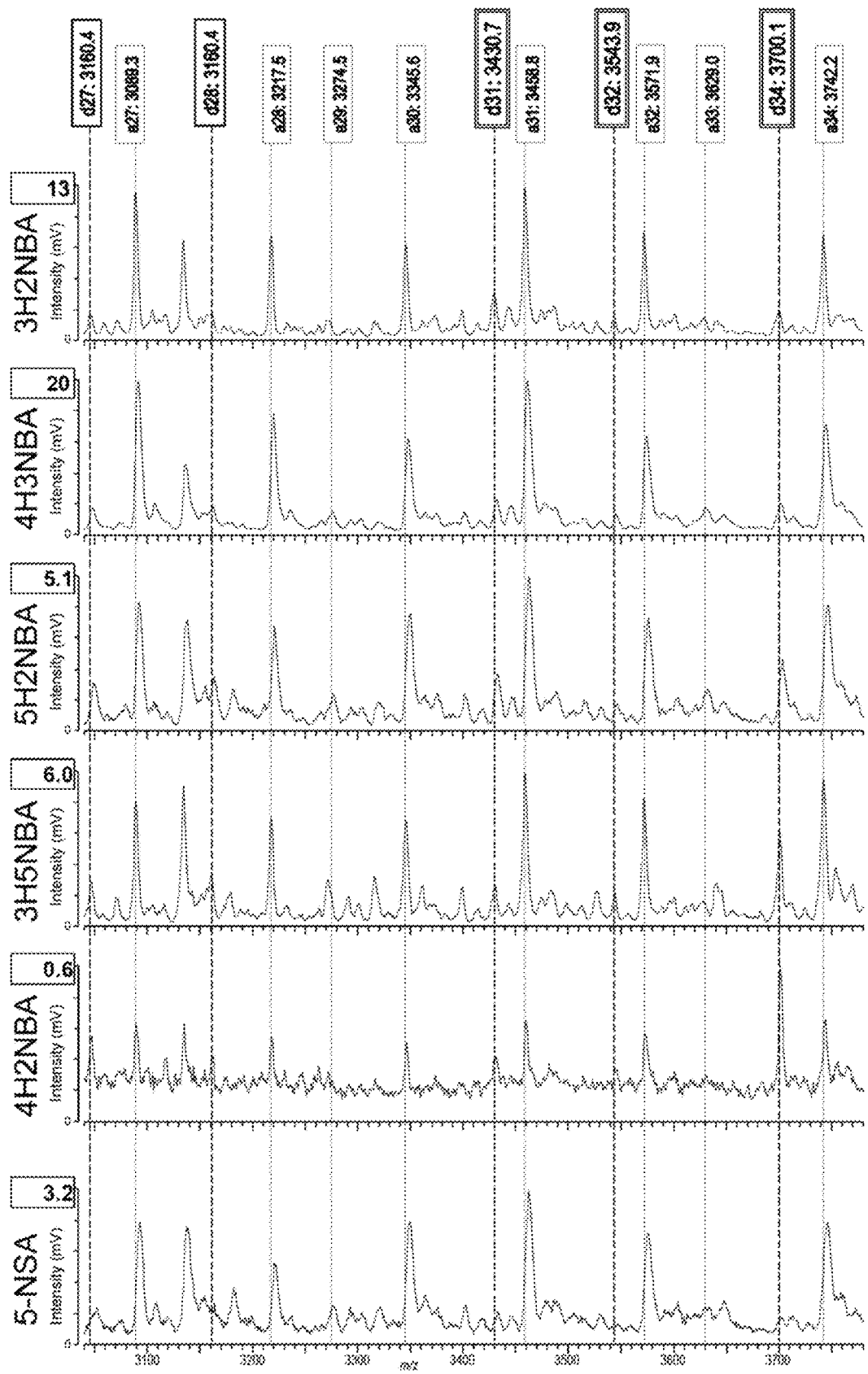
FIG. 7 is a partial enlarged view of a high mass region in FIG. 5.
Figure 8:
FIG. 8 is an ISD ion theoretical value list of Amyloid β [1-40].

FIG. 5 shows overall views of ISD mass spectra (m/z: 450-4450) of Amyloid β [1-40] when 3H2NBA (top row), 4H3NBA (second row), 5H2NBA (third row), 3H5NBA (fourth row), 4H2NBA (fifth row), or 5-NSA (bottom row) is used as a matrix, FIG. 6 is a partial enlarged view of a low mass region in FIG. 5 (m/z: 1320-2060), and FIG. 7 is a partial enlarged view of a high mass region in FIG. 5 (m/z: 3040-3780).

As shown in the spectra of FIG. 5, when 5-NSA was used, a large variety and a large quantity of cluster ions derived from, the matrix were detected in the low mass region, and it tends to be difficult to obtain sequence information in the low mass region. Further, as shown in FIG. 6, ion species other than a- and d-series ion species were detected in a relatively large quantity, and as shown in FIG. 7, detection of d-series ion species in a high mass region is particularly difficult, and thus, it tends to be difficult to obtain sequence information in the intermediate mass region and the high mass region.

In contrast, as shown in the spectra of the top row to the fifth row of FIGS. 6 to 7, when 3H2NBA, 4H3NBA, 5H2NBA, 3H5NBA, or 4H2NBA was used, all the a-series ion species, and all the d-series ion species (d17, d31, d32, d34) distinguishing between isoleucine (Ile, I) and leucine (Leu, L) were detected. Therefore, it is easy to obtain sequence information.

Example 3

Additional advantageous effects when 3H2NBA, 4H3NBA, 5H2NBA, 3H5NBA, or 4H2NBA is used as a matrix will be shown by referring to FIGS. 9(A) to 9(G).

FIG. 9(A) is a stereoscopic microphotograph showing an example of condition of a residue after drooping a 3H2NBA solution as a matrix, and a peptide sample solution of Amyloid β [1-40] on a sample plate, and drying the mixed solution. Similarly, FIG. 9(B) is a photograph obtained when 4H3NBA is used as a matrix. FIG. 9(C) is a photograph obtained when 5H2NBA is used as a matrix. FIG. 9(D) is a photograph obtained when 3H5NBA is used as a matrix. FIG. 9(E) is a photograph obtained when 4H2NBA is used as a matrix.

FIG. 9(F) is a stereoscopic microphotograph showing an example of condition of a residue after dropping a 5-NSA solution as a matrix, and a peptide sample solution of Amyloid β [1-40] on a sample plate, and drying the mixed solution. FIG. 9(G) is a photograph obtained when 1,5-DAN is used as a matrix.

Figure 9:
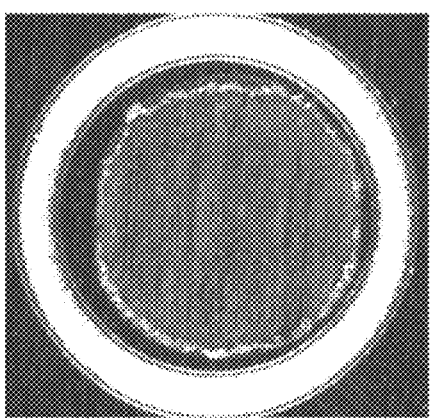
FIG. 9 shows stereoscopic microphotographs each showing an example of condition of a residue after dropping, on a sample plate, a peptide sample solution of Amyloid β [1-40] and a matrix solution using.
Figure 9:
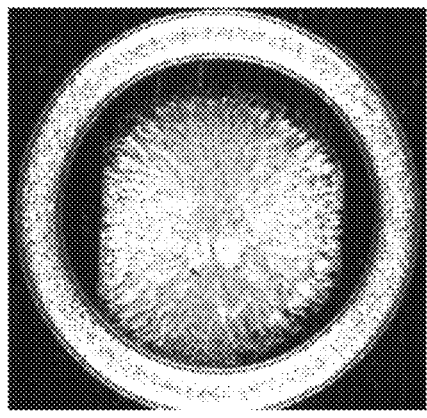
Figure 9:
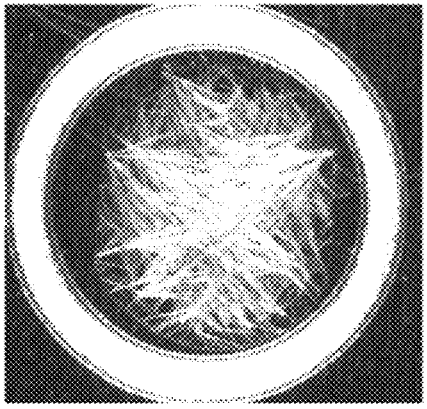
Figure 9:
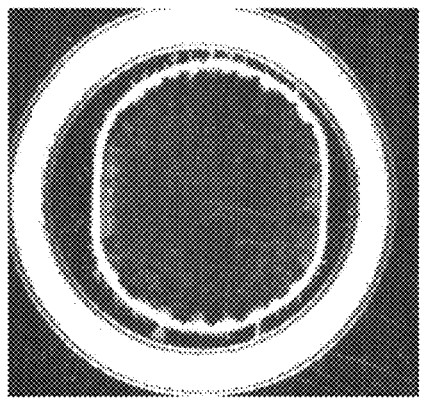
Figure 9:
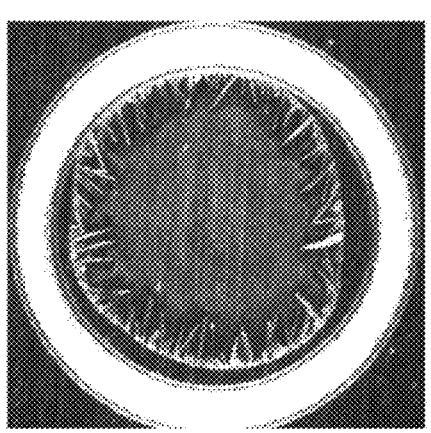
Figure 9:
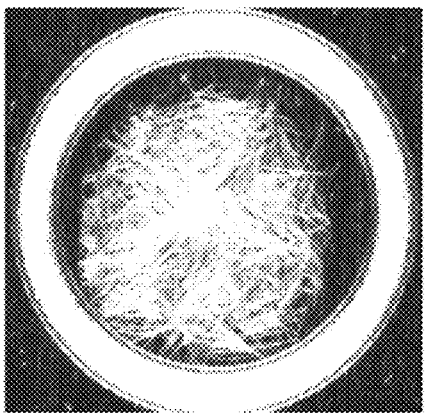
Figure 9:
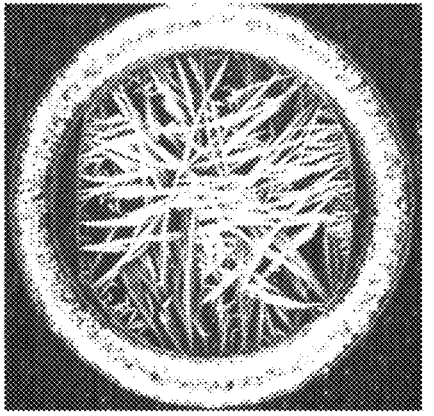

As shown in FIG. 9, when (A) 3H2NBA, (B) 4H3NBA, (C) 5H2NBA, (D) 3H5NBA, or (E) 4H2NBA was used as a matrix, the form inside the residue to be ionized was observed to be relatively uniform by a square Raster scan. In contrast, it was also observed that when (G) 1,5-DAN was used, an elongated crystal grew largely, and thus the form of the residue was nonuniform.

As shown in FIG. 9(F), when 5-NSA was used as a matrix, the form inside the residue to be ionized was observed to be relatively uniform by a square Raster scan as is the case with using (A) 3H2NBA, (B) 4H3NBA, (C) 5H2NBA, (D) 3H5NBA, or (E) 4H2NBA as a matrix, but the thickness of the residue tends to be large.

What is claimed is:

1. A method for specifically cleaving a Cα-C bond of a peptide backbone and/or a side chain bond of a protein or a peptide, comprising irradiating a protein or a peptide with laser light in the presence of at least one hydroxynitrobenzoic acid selected from the group consisting of:

3-hydroxy-2-nitrobenzoic acid:

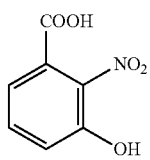
[Chemical formula 1]

4-hydroxy-3-nitrobenzoic acid:

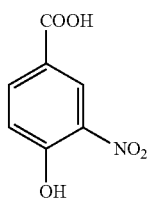
[Chemical formula 2]

5-hydroxy-2-nitrobenzoic acid:

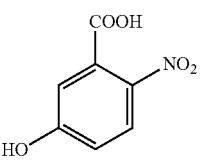
[Chemical formula 3]

3-hydroxy-5-nitrobenzoic acid:

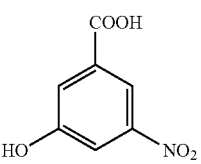
[Chemical formula 4]

and
4-hydroxy-2-nitrobenzoic acid:

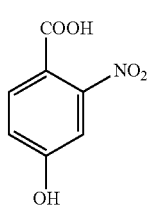
[Chemical formula 5]

to specifically cleave the Cα-C bond of the peptide backbone and/or the side chain bond, wherein the hydroxynitrobenzoic acid promotes the specific cleavage of the Cα-C bond of the peptide backbone and/or the side chain bond.

2. A method for determining an amino acid sequence of a protein or a peptide, comprising:

irradiating a protein or a peptide with laser light in the presence of at least one hydroxynitrobenzoic acid selected from the group consisting of:

3-hydroxy-2-nitrobenzoic acid:

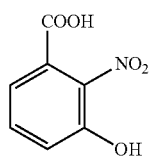
[Chemical formula 6]

4-hydroxy-3-nitrobenzoic acid:

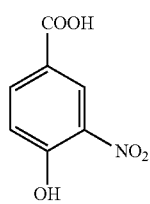
[Chemical formula 7]

5-hydroxy-2-nitrobenzoic acid:

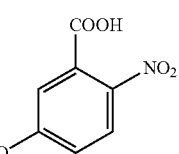
[Chemical formula 8]

3-hydroxy-5-nitrobenzoic acid:

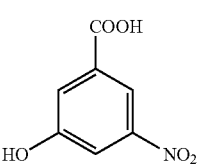
[Chemical formula 9]

and
4-hydroxy-2-nitrobenzoic acid:

[Chemical formula 10]

to specifically cleave a Cα-C bond of a peptide backbone and/or a side chain bond; and analyzing generated fragment ions by mass spectrometry, wherein the hydroxynitrobenzoic acid promotes the specific cleavage of the Cα-C bond of the peptide backbone and/or the side chain bond.

3. A method for determining an amino acid sequence of a protein or a peptide, comprising:

irradiating a protein or a peptide with laser light in the presence of at least one hydroxynitrobenzoic acid selected from the group consisting of 3-hydroxy-2-nitrobenzoic acid, 4-hydroxy-3-nitrobenzoic acid, 5-hydroxy-2-nitrobenzoic acid, 3-hydroxy-5-nitrobenzoic acid, and 4-hydroxy-2-nitrobenzoic acid as a matrix to specifically cleave a Cα-C bond of a peptide backbone and/or a side chain bond; and analyzing generated fragment ions by MALDI mass spectrometry, wherein the hydroxynitrobenzoic acid promotes the specific cleavage of the Cα-C bond of the peptide backbone and/or the side chain bond.

4. The method for determining an amino acid sequence of a protein or a peptide according to claim 2, wherein as the generated fragment ions, a-series ion species and/or x-series ion species are analyzed.

5. The method for determining an amino acid sequence of a protein or a peptide according to claim 2, wherein as the generated fragment ions, a-series ion species and d-series ion species are analyzed.

* * * * *